(12) United States Patent
Bouten et al.

(10) Patent No.: US 8,399,243 B2
(45) Date of Patent: Mar. 19, 2013

(54) METHOD OF MANUFACTURING A TISSUE-ENGINEERED PROSTHESIS

(75) Inventors: Carlijin V. C. Bouten, Eindhoven (NL); Anita Mol, Eindhoven (NL); Marcel C. M. Rutten, Eindhoven (NL); Simon P. Hoerstrup, Zurich (CH); Frank P. T. Baaijens, Eindhoven (NL)

(73) Assignees: Universitaet Zuerich, Zurich (CH); Technische Universiteit Eindhoven, Eindhoven (NL)

( * ) Notice: Subject to any disclaimer, the term of this patent is extended or adjusted under 35 U.S.C. 154(b) by 933 days.

(21) Appl. No.: 11/816,271

(22) PCT Filed: Feb. 1, 2006

(86) PCT No.: PCT/EP2006/000877
§ 371 (c)(1),
(2), (4) Date: Feb. 15, 2008

(87) PCT Pub. No.: WO2006/087101
PCT Pub. Date: Aug. 24, 2006

(65) Prior Publication Data
US 2008/0145920 A1    Jun. 19, 2008

(30) Foreign Application Priority Data

Feb. 17, 2005    (EP) .................................. 05003425

(51) Int. Cl.
*A01N 1/00*    (2006.01)
*A01N 1/02*    (2006.01)

(52) U.S. Cl. .... 435/284.1; 435/1.1; 435/1.2; 435/285.1; 435/289.1; 435/293.1; 435/297.2; 435/299.1; 435/304.1; 435/305.1; 600/36; 623/915; 623/916; 623/921

(58) Field of Classification Search ............... 435/284.1, 435/1.1, 1.2, 285.1, 289.1, 293.1, 297.2, 435/299.1, 304.1, 305.1; 600/36; 623/915, 623/916, 921
See application file for complete search history.

(56) References Cited

U.S. PATENT DOCUMENTS
4,562,597 A * 1/1986 Possis et al. .................. 128/898
(Continued)

FOREIGN PATENT DOCUMENTS
DE    19828726 A1    6/1998
DE    199919625 A1    4/1999
(Continued)

OTHER PUBLICATIONS

Barron, V., et al., "Bioreactors for Cardiovascular Cell and Tissue Growth: A Review," Annals of Biomedical Engineering, vol. 31, pp. 1017-1030, 2003.
(Continued)

*Primary Examiner* — Nathan Bowers
(74) *Attorney, Agent, or Firm* — Sughrue Mion, PLLC (57) ABSTRACT

Developing heart valves are exposed to dynamic strains by applying a dynamic pressure difference over the leaflets. The flow is kept to a minimum, serving only as a perfusion system, supplying the developing tissue with fresh nutrients. Standard heart valves were engineered based on B trileaflet scaffolds seeded with cells isolated from the human saphenous vein. Tissue compaction is constrained by the stent, inducing increasing pre-strain in the tissue. The dynamic strains the tissues are exposed to via the dynamic pressure difference, are estimated using finite element methods based on the mechanical properties of the neo-tissue, in order to get inside into the strain distribution over the leaflet.

10 Claims, 8 Drawing Sheets

U.S. PATENT DOCUMENTS

| | | | |
|---|---|---|---|
| 5,662,711 | A * | 9/1997 | Douglas .......................... 604/9 |
| 5,792,603 | A * | 8/1998 | Dunkelman et al. ........... 435/1.2 |
| 5,843,781 | A | 12/1998 | Ballermann et al. |
| 5,846,828 | A | 12/1998 | Peterson et al. |
| 5,855,610 | A | 1/1999 | Vacanti et al. |
| 5,899,937 | A | 5/1999 | Goldstein et al. |
| 6,174,719 | B1 * | 1/2001 | Elizondo et al. ........... 435/284.1 |
| 6,348,069 | B1 | 2/2002 | Vacanti et al. |
| 6,416,995 | B1 * | 7/2002 | Wolfinbarger ............. 435/289.1 |
| 6,881,569 | B2 | 4/2005 | Perry et al. |
| 6,960,427 | B2 | 11/2005 | Haverich et al. |
| 7,732,125 | B2 | 6/2010 | Haverich et al. |
| 7,744,526 | B2 | 6/2010 | McAllister et al. |
| 2001/0051824 | A1 | 12/2001 | Hopkins et al. |
| 2004/0219659 | A1 * | 11/2004 | Altman et al. ............. 435/284.1 |
| 2006/0122695 | A1 | 6/2006 | Atala |
| 2006/0223049 | A1 * | 10/2006 | Dancu et al. ................... 435/1.2 |

FOREIGN PATENT DOCUMENTS

| | | |
|---|---|---|
| DE | 10053014 A1 | 10/2000 |
| EP | 0320441 A1 | 10/1988 |
| EP | 1339356 B1 | 4/2005 |
| EP | 2075015 A1 | 7/2009 |
| FR | 2290182 A1 | 6/1976 |
| WO | WO 82/03764 A1 | 11/1982 |
| WO | 00/37123 A1 | 6/2000 |
| WO | WO 01/82840 A1 | 11/2001 |
| WO | 02/14480 A3 | 2/2002 |
| WO | 02/33052 A3 | 4/2002 |
| WO | 02/35992 A3 | 5/2002 |
| WO | 02/40076 A1 | 5/2002 |
| WO | 02/065952 A3 | 8/2002 |
| WO | 03/078597 A3 | 9/2003 |
| WO | 03/082007 A3 | 10/2003 |
| WO | WO 2004/018008 A1 | 3/2004 |

OTHER PUBLICATIONS

Dumont, Kris, et al., "Design of a New Pulsatile Bioreactor for Tissue Engineered Aortic Heart Valve Formation," Artif. Organs, vol. 26, No. 8, 2002.

Engelmayr Jr., George C., et al., "A Novel Bioreactor for the Dynamic Flexural Stimulation of Tissue Engineered Heart Valve Biomaterials," Biomaterials, vol. 24, No. 14, Jun. 2003, pp. 2523-2532.

Hoerstrup, Simon P., et al., "Tissue Engineering of a Bioprosthetic Heart Valve: Stimulation of Extracellular Matrix Assesed by Hydroxyproline Assay," ASAIO Journal 1999, 397-402.

Hoerstrup, Simon P., et al., "New Pulsatile Bioreactor for In Vitro Formation of Tissue Engineered Heart Valve," Tissue Engineering, vol. 6, No. 1, Feb. 2000, pp. 75-79.

Sodian, Ralf, et al., "New Pulsatile Bioreactor for Fabrication of Tissue-Engineered Patches," Journal of Biomedical Materials Research, vol. 58, No. 4, 2001, pp. 401-405.

Sodian, Ralf, et al., "Tissue Engineering of Heart Valves: In Vitro Enperiences," The Annals of Thoracic Surgery, vol. 70, No. 1, Jul. 2000, pp. 140-144.

Sodian, Ralf et al., "Application of Stereolithography for Scaffold Fabrication for Tissue Engineered Heart Valves," ASAIO Journal, vol. 48, No. 1, Jan. 2002, pp. 12-16.

Zund, Gregor et al., "Tissue Engineering: A New Approach in Cardiovascular Surgery; Seeding of Human Fibroblasts Followed by Human Endothelial Cells on Resorbable Mesh," European Journal of Cardio-Thoracic Surgery, vol. 13, Feb. 1998, pp. 160-164.

Breuer Ck, Shin'oka T, Tanel RE, Zund G, Mooney DJ, Ma PX, Miura T, Colan S, Langer R, Mayer JE, Vacanti JP. Tissue engineering lamb heart valve leaflets. Biotechnol Bioeng. Jun. 5, 1996;50(5):562-7. Publ. Date: May 6, 1996.

Hill, Ronald J. et al., Quantitation of Types I and III Collagens in Human Tissue Samples and Cell Culture by Cyanogen Bromide Peptide Analysis, Analytical Biochemistry 141, 83-93 (1984).

Hoerstrup et al, Functional living Trileaflet . . . , Circulation 2000; 102;44-49; Publ. date Jul. 11, 2000.

Hoerstrup SP, Sodian R, Sperling JS, Vacanti JP, Mayer JE Jr. New pulsatile bioreactor for in vitro formation of tissue engineered heart valves. Tissue Eng. Feb. 2000;6(1):75-9. Publ. Date: Jun. 2000.

Hoerstrup SP, Zünd G, Ye Q, Schoeberlein A, Schmid AC, Turina MI. Tissue engineering of a bioprosthetic heart valve: stimulation of extracellular matrix assessed by hydroxyproline assay. ASAIO J. Sep.-Oct. 1999;45(5):397-402. Publ. Date: Oct. 1999.

Hoerstrup, Simon P., et al, Functional Grown in Tissue-Engineered Living, Vascular Grats: Follow-Up at 100 Weeks in a Large Animal Model, Journal of American Heart Association; Circulations 2006; 114; 159-166.

Kanda K, Matsuda T. Behavior of arterial wall cells cultured on periodically stretched substrates. Cell Transplant. Nov.-Dec. 1993;2(6):475-84. Publ. Date: Nov. or Dec. 1993.

Mooney DJ, Breuer C, McNamara K, Vacanti JP, Langer R. Fabricating tubular devices from polymers of lactic and glycolic Acid for tissue engineering. Tissue Eng. 1995 Summer;1(2):107-18. Publ. Date: Feb. 1995.

Mooney DJ, Organ G, Vacanti JP, Langer R. Design and fabrication of biodegradable polymer devices to engineer tubular tissues. Cell Transplant. Mar.-Apr. 1994;3(2):203-10.Publ. Date: Mar. or Apr. 1994 (?).

Shinoka T, Breuer CK, Tanel RE, Zund G, Miura T, Ma PX, Langer R, Vacanti JP, Mayer JE Jr. Tissue engineering heart valves: valve leaflet replacement study in a lamb model. Ann Thorac Surg. Dec. 1995;60(6 Suppl):S513-6. Publ. Date: Presentation Apr. 20-22, 1995 in Boston.

Shinoka T, Ma PX, Shum-Tim D, Breuer CK, Cusick RA, Zund G, Langer R, Vacanti JP, Mayer JE Jr. Tissue-engineered heart valves. Autologous valve leaflet replacement study in a lamb model. Circulation. Nov. 1, 1996;94(9 Suppl):II164-8 Publ. Date: Jan. 11, 1996.

Sodian, et al, Early in vivo experience with Tissue-Engineered Trileaflet Heart Valves, Circulation 2000; 102, 22-29; Publ. date Jul. 11, 2000.

Zünd et al; The in vitro construction of a tissue engineered bioprosthetic heart valve, European Journal of Cardio-Thoracic Surgery, 1997; 11:493-497; Publ. Date: Presented Sep. 24-27, 1995 in Paris.

Zünd G, Hoerstrup SP, Schoeberlein A, Lachat M, Uhlschmid G, Vogt PR, Turina M. Tissue engineering: a new approach in cardiovascular surgery: Seeding of human fibroblasts followed by human endothelial cells on resorbable mesh. Eur J Cardiothorac Surg. Feb. 1998;13(2):160-4. Publ. Date: Presented Sep. 28-Jan. 10, 1997.

* cited by examiner

METHOD OF MANUFACTURING A TISSUE-ENGINEERED PROSTHESIS

CROSS-REFERENCE TO RELATED APPLICATIONS

This application is the United States National Phase of PCT/EP2006/000877, filed Feb. 1, 2006, which claims priority to European Patent Application No. 05003425.5, filed Feb. 17, 2005.

The invention is directed to a method of manufacturing a tissue-engineered prosthesis having at least in an open condition a flow passage, especially human heart valves. The invention is also directed to a respective bioreactor.

Such a method is known from WO2004/018008 A1 and WO2004/101012 A1. The latter also discloses a bioreactor for producing tissue prosthesis, particularly a heart valve.

Mechanical conditioning in a bioreactor profoundly affects the composition and structure and hence mechanical properties of tissue engineered heart valves. Up to now, the methods and bioreactors developed for culturing heart valves are flow-based and mimic the normal heart valve opening and closing behaviour. This method of conditioning has resulted in enhanced tissue formation and mechanical properties, however, yet insufficient to serve as systemic heart valve replacement such as an aortic heart valve replacement.

In cardiovascular tissue engineering, stimulation of tissue formation by mechanical conditioning has proven to be a useful tool for development of functional cardiovascular structures enabling growth, repair, and remodeling. The main ways of conditioning a developing tissue are by applying either flow or strain, or a combination of both. Various bioreactors have been developed in the past years to apply specific conditioning protocols to growing cardiovascular structures.

Bioreactors that use flow as the main mechanical stimulus are, for example, the bioreactors developed by Williams and Wick (2004) and Narita et al. (2004) to engineer blood vessels. Furthermore, a pulse duplicator system has been developed by Hoerstrup et al. (2000a,b) to grow heart valves as well as blood vessels, modified by Sodian et al. (2001, 2002b) to include the seeding procedure. Bioreactors that use strains as the main mechanical cue are e.g. the bioreactors developed by Niklason et al. (1999, 2001) and Seliktar et al. (2000) for tissue engineering of blood vessels. In these bioreactors, the tissue is exposed to dynamic strains by applying intraluminal pulsatile pressures via an inflatable silicone tube. Niklason et al. (1999, 2001) apply dynamic strains of about 5%, while Seliktar et al. (2000) use larger strains of about 10%. For myocardial tissue, a comparable bioreactor is developed by Gonen-Wadmany et al. (2004) applying dynamic strains (0-12%) to the developing tissue by pulsatile inflation of a silicone bulb, to which the tissue is attached. The flow applied to the tissues cultured in these strain-based bioreactors can be kept to a minimum and are mainly induced by medium circulation or the movement of the tissue itself. In another type of bioreactors, the physiological environment of the cardiovascular structure is mimicked, including both flow and strain. These bioreactors can be used for testing native tissues, as well as for tissue engineering and subsequent functionality testing. A bioreactor in which the physiological pressure waveforms, present in a blood vessel, can be applied is the system developed by McCulloch et al. (2004). A bioreactor in which physiological pressure waveforms can be applied in combination with physiological flows is developed by Thompson et al. (2002). As blood vessels are exposed to longitudinal strains in-vivo as well, Mironov et al. (2003) developed a bioreactor that exposes developing blood vessels to a physiological environment including dynamic longitudinal strains. Hildebrand et al. (2004), Dumont et al. (2002), and Rutten et al. (2005) have developed bioreactors, in which the exact physiological conditions of a heart valve in-vivo can be applied, with the latter providing the possibility to visualize valve function using MRI. Despite these efforts, the question still remains to what extent the developing tissue should be exposed to mechanical cues and which mechanical cues are optimal for tissue development.

The cells in the tissue engineered structures are responsible for the formation of the extracellular matrix and via mechanical conditioning they can be stimulated to produce larger amounts of extracellular matrix. Apart from the nature and magnitude of the mechanical cues, the cellular (pheno)type as well as the culture conditions (either 2D or in a 3D environment) affect the cellular responses to mechanical loading (Dethlefsen et al., 1996; Ueba et al., 1997; Watase et al., 1997; Kim et al., 1999; Chapman et al., 2000; O'Callaghan and Williams, 2000; Kim and Mooney, 2000; Jockenhoevel et al., 2002; Lee et al., 2002; Engelmayr et al., 2005). Human saphenous vein cells were chosen as a cell source for tissue engineering of human heart valve leaflets. Not only do they represent an easily accessible cell source, they were also shown to be more sensitive to mechanical cues compared to human arterial derived cells (Dethlefsen et al., 1996; Schnell et al., 2001). Although the optimal conditioning procedure for this specific cell type still has to be determined, increased extracellular matrix formation has been demonstrated in engineered valve leaflet tissue-equivalents cultured with these cells using dynamic strains (Mol et al., 2003). It is, therefore, hypothesized that the optimal conditioning protocol involves dynamic strains to stimulate matrix production by the seeded vascular cells. An initial low shear stress environment combined with exposure of the developing tissue to physical stimuli has been suggested by Barron et al. (2003) to be advantageous for initial tissue development. Shear stresses, by application of flows, will most likely start to play a significant role at a later stage when the leaflets are seeded with endothelial cells to provide a non-thrombogenic surface layer, stabilizing the underlying tissue prior to implantation (Nackman et al., 1998; Weston and Yoganathan, 2001).

It is the object of the present invention to improve the mechanical properties of tissue-engineered prosthesis.

The object is achieved by a method of manufacturing a tissue-engineered prosthesis, having at least in an open condition a flow passage, especially human heart valves, comprising the steps of:

Placing a seeded 3D scaffold in a bioreactor chamber

Providing at least one perfusion flow of a nutrient medium in the bioreactor chamber to supply said seeded 3D scaffold and/or a thereon developing tissue with nutrients whereby a flow passage of the seeded 3D scaffold and/or the thereon developing tissue in relation to the flow passage of the finished prosthesis is restricted or zero;

Applying in addition a dynamic pressure difference over the 3D scaffold and/or thereon developing tissue, depending on the condition and/or stage of tissue development to create strain in the 3D scaffold and/or thereon developing tissue; and opening the restricted or zero flow passage to its finished size.

Contrary to the former flow-based methods, the present invention provides for a strain-based approach. In order to develop sufficient strain in the 3D scaffold and/or thereon developing tissue the developing prosthesis is exposed to dynamic strains by applying a dynamic pressure difference.

The strain-based approach has shown to render tissue-engineered prosthesis with superior tissue formation and organisation and hence improved mechanical properties. The appropriate strain can be provided by restricting or closing the flow passage of the developing prosthesis during the duration stay in the bioreactor chamber. The restriction or closure of the flow passage during tissue development is opened to its final size as usual for the respective prosthesis, especially human heart valve. For example, only a small opening could be present allowing only for a minimum perfusion flow of a nutrition medium from the one side of the prosthesis to the other. In case the flow passage is completely closed two separate perfusion flows could be provided, one on each side of the developing prosthesis. With heart valves the restriction may be achieved by coaptation of the leaflets.

The goal of one embodiment is to set up a basic concept to engineer human heart valve leaflets using dynamic strains in combination with minimized flows to stimulate extracellular matrix formation. This is a novel approach as all currently used conditioning approaches for tissue engineering of heart valves concentrate on the application of pulsatile flows, with none or limited tissue straining. For this purpose, a new bioreactor system is developed, the Diastolic Pulse Duplicator (DPD), to deliver dynamic strains to the heart valve leaflets by applying a dynamic pressure difference over the closed leaflets. Requirements for such a bioreactor system are: 1) simplicity in its use, 2) sized small to save on culture medium and incubator space, 3) usage of biocompatible materials, 4) maintenance of sterility over prolonged periods of time, and 5) the ability to monitor and control the applied transvalvular pressure. As a stented valve geometry is used in this study, compaction-induced prestrain develops in the leaflets as tissue compaction, common in growing and healing tissues, is constrained by the rigid stent. Medium is circulating in the DPD at low speed (4 ml/min) to provide oxygen and fresh nutrients to the developing tissue and to remove waste products.

The feasibility of the strain-based approach for human heart valve tissue engineering is demonstrated. Tissue formation and mechanical properties of leaflets exposed to dynamic strains in the DPD and compaction-induced prestrain by the stent were compared with leaflets exposed to compaction-induced prestrain only. The latter leaflets were cultured in the DPD with low-speed medium circulation without application of a dynamic pressure difference. As controls, unloaded rectangular-shaped valve leaflet tissue-equivalents, in which compaction was not constrained, were used. The valve scaffolds were prepared from a non-woven PGA fiber mesh, coated with P4HB. Fibrin was used as a carrier for the human saphenous vein cells to ensure homogeneous cell distribution throughout the scaffold and to render a compact structure suitable for mechanical conditioning (Mol et al., 2005). The levels of compaction induced prestrain were estimated, as well as the strain distribution in the leaflets resulting from the dynamic transvalvular pressure applied in the DPD, the latter using numerical analyses.

In one embodiment the restricted or zero flow passage is at least 20%, preferably 50% or more, smaller than the flow passage of the finished prosthesis. A dynamic pressure pulse creates more strain on the 3D scaffold or developing tissue if a compensation flow through the flow passage is kept to a minimum or zero. In case the restriction is formed by means of a coaptation area on the individual leaflets the flow passage is chosen sufficient to either frequently of occasionally open the valve.

In a further variant, the at least one perfusion flow is less than 50 ml/min, preferably less that 5 ml/min. The perfusion flow is kept to a minimum and the opening in the 3D scaffold and/or developing tissue should only be sufficiently sized to allow this small perfusion flow through it and only having few influence on the creation of the pressure difference.

It is of further advantage if the at least one perfusion flow has substantially no pulsation. Especially the mimic of the normal flow behaviour through the prosthesis should not be imitated. In case a roller pump is used, only the influence of the usual operation of this pump is present and no additional pulsation. The flow should be kept substantially constant.

In a further embodiment the pressure difference is substantially zero at the beginning, subsequently increasing up to a mean peak pressure difference and thereafter decreasing to the end of the duration of stay of the 3D scaffold and/or thereon developing tissue in the bioreactor chamber. First the tissue is given time to develop without substantial strain. Then the mean distribution of strain is increased and after reaching a mean peak pressure difference after a certain time it decreases to the end of the duration of stay in the bioreactor.

A mean peak pressure difference, averaged for 24 hours is above 25 mmHg, preferably above 45 mmHg. This assures that a significant amount of strain is provided which enhances tissue formation and organisation.

Furthermore, the mean pressure difference could be, over a time period, which is 30-70%, preferably 45-55%, of the duration of stay in the bioreactor substantially zero. Such a time period gives tissue sufficient time for development on the 3D scaffold.

According to another embodiment the mean peak pressure difference averaged for 24 hours is reached after 60%, preferably after 70%, of the duration of stay in the bioreactor. As can be seen, the strain based influence in the tissue formation and organisation is made in the second half of the duration of stay in the bioreactor.

A modulated pressure difference could be used for a specific time period, preferably 24 hours, to provide a respective strain distribution in that specific time period. The pressure difference could almost only be modulated with regard to a mean pressure difference per time period but also within the respective time period so as to gain a mean pressure difference.

The dynamic pressure difference could have a frequency or 0.1-10 Hz, preferably 1 Hz. The dynamic pressure differences have a frequency, which is similar to an average heart sequence, but not the flow through the prosthesis is mimicked but the strain in the prosthesis is provided in this frequency.

The invention is further directed to a bioreactor for manufacturing a tissue-engineered prosthesis having at least in an open condition a flow passage, especially human heart valves, comprising:

A bioreactor chamber for inserting therein a seeded 3D scaffold, at least one perfusion flow means to provide at least one perfusion flow of a nutrient medium in the bioreactor chamber, in addition pressurising means to apply a dynamic pressure difference over the seeded 3D scaffold and/or thereon developing tissue to create strain in the 3D scaffold and/or thereon developing tissue, the pressuriser means having a compressible and decompressible tubing in flow connection with the bioreactor chamber.

The perfusion flow means and the additional pressurising means are preferably independent from one another so that they apply a dynamic pressure difference overlaying the at least one perfusion flow which usually has no pulsation. In order to not have a contamination of the nutrient medium a pressure pulse from the outside of the tubing is applied. The tubing is compressible and returns back to its initial shape after pressure release.

In a preferred embodiment, at least a portion of the compressible and decompressible tubing is placed in a cylinder surrounding the outer surface of said portion of the tubing and having a port for flow of a compressed fluid, preferably air, into the cylinder. The cylinder is preferably manufactured from rigid material so that sufficient pressure can be provided within the space between the cylinder and the tubing.

A magnet valve could be provided which is in flow communication with the port of the cylinder to control the flow of the compressed fluid into the cylinder. The magnet valve could also control the outflow of the fluid out of the cylinder. A constant supply pressure could be provided which is modulated by the magnet valve so that within the cylinder the predetermined pressure is present. This allows for an easy and cost efficient modulation of the pressure.

Furthermore, a compliance chamber could be provided in flow communication with the bioreactor chamber to compensate for the displacement of the nutrient medium due to the pressure difference. Especially below the developing prosthesis some of the nutrient medium is displaced. Due to only a minimum of perfusion flow, the displaced volume of the nutrient volume has to be compensated by the compliance chamber. After pressure release the displaced nutrient medium flows back out of the compliance chamber and into the respective portion of the bioreactor chamber. The overall flow rate of the nutrition medium is not increased.

In a further embodiment, the bioreactor chamber has a first and a second portion each provided with a pressure sensor and holding means for holding the 3D scaffold and/or the thereon-developing tissue is positioned between the first and second portion. With these two sensors the pressure difference from one side of the developing prosthesis to the other side can be measured.

In the following, an embodiment of the present invention is described in detail. The following description should not, however, restrict the claims. The claims should be understood in their broadest meaning. The figures show:

PREPARATION OF THE LEAFLET TISSUES

The Heart Valve Scaffold

Figure 1A:
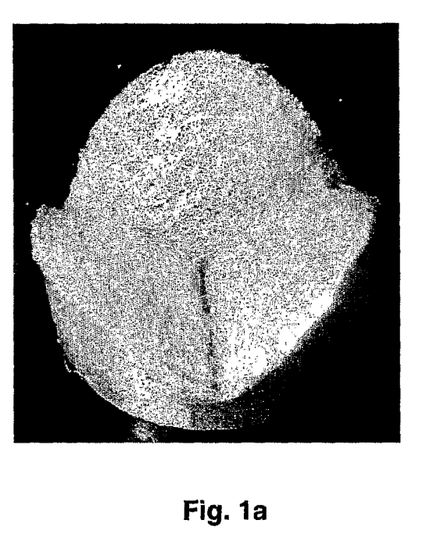
FIGS. 1a, 1b: Photographs of the valve scaffold, bottom view (a) and top view (b).
Figure 1B:
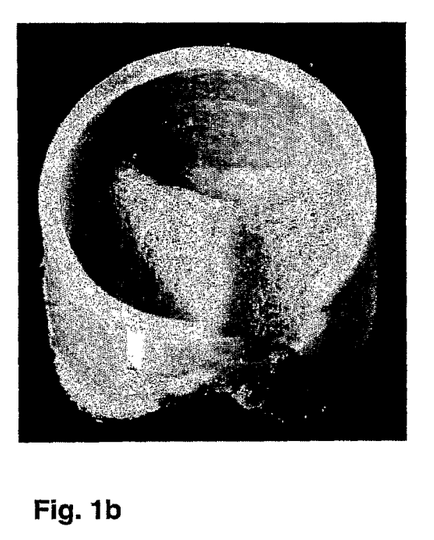

Trileaflet heart valve scaffolds were fabricated on a Fastacryl R° stent. The two components, Fastacryl powder and fluid (PMMA and MMMA, Vertex-dental, the Netherlands) were mixed, poured into a mold, and allowed to polymerize for 30 minutes. After complete polymerization, the stent was released from the mold. Anatomically shaped leaflets, including coaptation areas, were cut out of non-woven polyglycolic acid meshes (PGA; thickness 1.0 mm; specific gravity 69 mg/cm3; Cellon, Luxembourg). The leaflets were coated with a thin layer of poly-4-hydroxybutyrate (P4HB; MW 1×106; TEPHA Inc., Cambridge, USA) as described before (Hoerstrup et al., 2000a). Before evaporation of the solvent, the leaflets were positioned onto a teflon mold in the shape of a trileaflet heart valve. The fastacryl stent was placed on top. By action of the solvent, dissolving the surface layer of the stent, the leaflets were fixed to the stent. After evaporation of the solvent, the valve scaffold including the stent was removed from the mold (FIGS. 1a,1b). The valve scaffolds were further dried under vacuum overnight to remove solvent remnants, after which they were sterilized using ethylene oxide. The leaflets contain coaptation to ensure closure of the valve.

Seeding Procedure

Cells harvested from the human vena saphena magna and expanded using regular cell culture methods were used (Schnell et al., 2001). The medium to culture these cells consisted of DMEM Advanced (Gibco, USA), supplemented with 10% Fetal Bovine Serum (FBS; PAN Biotech, Germany), 1% GlutaMax (Gibco, USA), and 0.1% gentamycin (PAN Biotech, Germany). The medium used for seeding and subsequent tissue culture contained 0.3% gentamycin and additional L-ascorbic acid 2-phosphate (0.25 mg/ml; Sigma, USA) to promote extracellular matrix production. The scaffolds were placed in medium overnight before seeding to facilitate cell attachment by deposition of proteins. The seeding was performed per leaflet using fibrin as a cell carrier (Mol et al., 2005). Briefly, the cells were suspended in a sterile thrombin solution (10 IU/ml medium; Sigma, USA) in a volume that equals half the void volume of the scaffold (0.5× length×width×thickness). The cells in thrombin were mixed with an equal amount of sterile fibrinogen solution (10 mg actual protein/ml medium; Sigma, USA) and dripped onto the scaffold. The fibrin solution was taken up by the scaffold and remained inside due to polymerization of the fibrin gel. The leaflets were seeded with a density of 4-5 million cells (passage 6-7) per cm2 of scaffold. The seeded valve scaffolds were allowed to polymerize for 20 minutes in an incubator (37±C and 5% CO2) before placement into the DPD.

The Diastolic Pulse Duplicator (DPD)

Description of the DPD

Figure 2A:
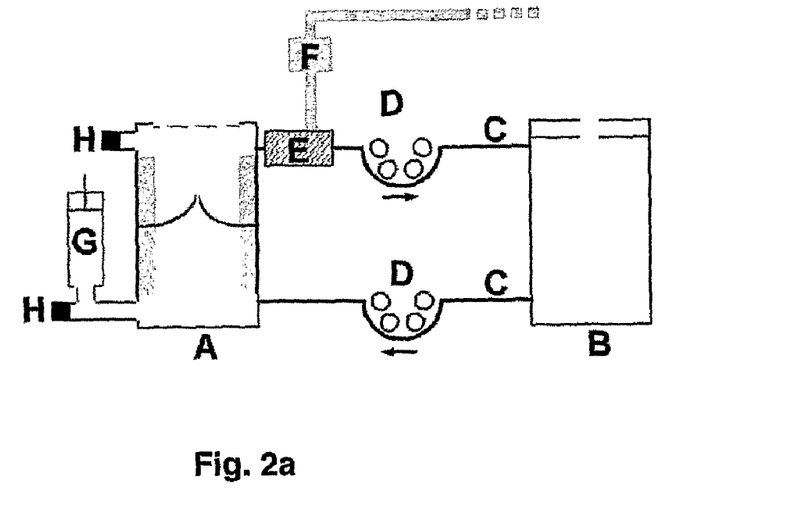
FIGS. 2a, 2b: Schematic drawing of one DPD and its function (a) and a photograph of six DPD systems in use simultaneously (b).

One DPD consists of a bioreactor [A], in which the valve is cultured, and a medium container [B]. They are connected to each other via two parallel tubing series [C], which run through a roller pump [D]. Part of the upper tubing consists of a thicker tube placed in a polycarbonate cylinder [E]. Compressed air can be released into this cylinder, via a magnet valve [F], to compress and decompress the tube, resulting in a pressure difference over the leaflets. A syringe [G], placed on the bioreactor, serves as a compliance chamber. The pressures upstream and downstream of the leaflets is monitored using pressure sensors [H].

Figure 2B:
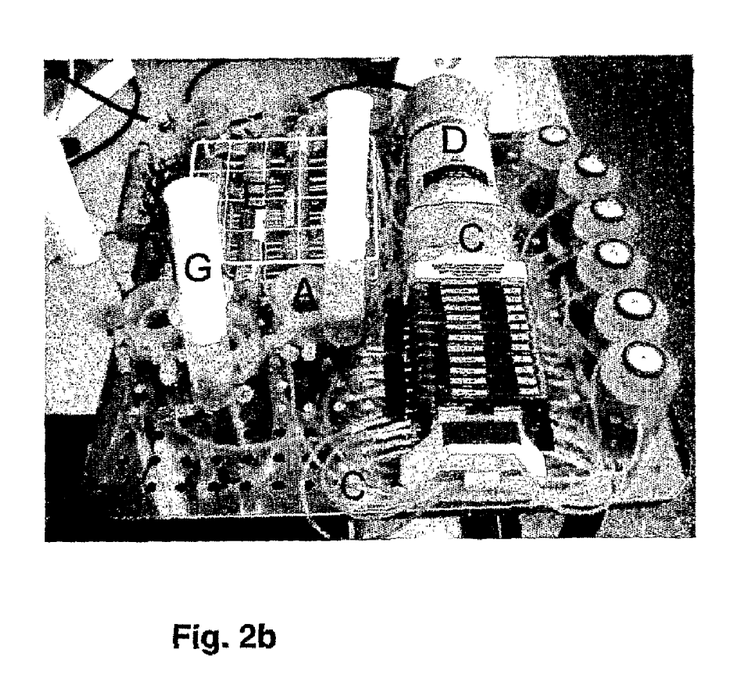

Each DPD consists of two components as shown in FIG. 2(a): a bioreactor (height=9 cm, diameter=6 cm), in which the valve is cultured, and a medium container of similar dimensions, both fabricated from polycarbonate (KUBRA Kunststoffen, The Netherlands). The bioreactor itself consists of two parts, the upper part containing a glass window (Melles Griot B V, The Netherlands) for visualization of the valve, and a lower part, which can be screwed together. Silicone rings (van der Heijden, The Netherlands) were used to seal all components. The bioreactor and the medium container are connected via two parallel silicone tubing series (Rubber, the Netherlands). Polypropylene connector parts (Neolab, Milispec Int., The Netherlands) were used to secure the tubing. Both tubing series run through a roller pump (Master®exr, ColeParmer, USA). Part of the upper tubing series consists of a thicker silicone tube placed in a polycarbonate cylinder, with a connection to tubing suitable to withstand air under pressure (Festo, The Netherlands). This compressed-air tubing is connected to a compressed-air tap (7 bar). The air pressure is reduced to 2 bar and runs through a proportional magnet valve (Festo, The Netherlands) into the polycarbonate cylinder. The complete DPD is sterilized by ethylene oxide and is placed inside an incubator, together with the roller pump. Up to six DPDs can be placed onto one shelf of a normal sized incubator as shown in FIG. 2 (b).

Functioning of the DPD

About 75 ml of medium is circulating from the medium container, through the bioreactor, and back into the medium container, via the roller pump at very low speed (4 ml/min) to supply fresh nutrients to and to remove waste products from the developing valve tissue. A sterile filter (0.2 μm, Schleicher & Schuell Bioscience, Germany) is placed in the lid of the medium container to oxygenate the circulating medium. About 25 ml of medium is present in the bioreactor and the tubing series, and the remaining 50 ml is present in the medium container and can be changed easily. To apply a dynamic pressure difference over the leaflets, the silicone tube in the polycarbonate cylinder is compressed and decompressed by the air coming from the proportional magnet valve. The transvalvular pressure generated over the valve leaflets is controlled via a programmable multi-IO-card using LabView software (National Instruments, USA). The shape and frequency of the pressure wave is programmed for an optimal transvalvular pressure. A syringe, connected to the lower part of the bioreactor, filled with 10 ml of medium and 40 ml of air, serves as compliance chamber. Pressure sensors (BD, Belgium), connected to both the lower and upper part of the bioreactor, are used to measure the pressure upstream (at the ventricular side) and downstream (at the arterial side) of the leaflets. Using the same multi-IO-card and software, the dynamic pressure difference could be monitored and logged.

Sterility and Biocompatibility

To prove maintained sterility over several weeks, the DPD was sterilized by ethylene oxide and filled with 75 ml of culture medium without the addition of gentamycin. The system was fully functional for a period of three weeks. During the testing period, a culture flask filled with culture medium, without gentamycin, served as control. The medium in the medium container was changed every 3-4 days as well as two thirds of the medium in the culture flask. The medium was checked microscopically for contamination and was stored at −20° C. until further use.

In order to ensure that the materials used in the DPD are suitable for cultivation of heart valves and that no toxic components are being released, a biocompatibility test was performed using the medium that was stored during the sterility test. Human saphenous vein cells were seeded into 24 wells plates (30.000 cells/well) and left overnight to attach and spread in an incubator in normal cell culture medium. The next day, the normal cell culture medium was replaced by the medium of the sterility test that had circulated through the DPD and the control medium (five wells per test group). The medium stored after the first four medium changes, as well as the control medium from the culture flask, was used. The cells were allowed to grow for three subsequent days, after which the metabolic activity of the cells, as a measure for viability, was determined using an MTT test (Mosmann, 1983). Briefly, MTT (Sigma, USA) in solution (5 mg/ml in PBS) was diluted in medium and added to the cells. After one hour of incubation at $37 \pm C$ and 5% $CO_2$, metabolic active cells had converted the MTT salt into purple crystals located inside the cells. Isopropanol (VWR International, USA), containing 10% formic acid (Sigma, USA) was added to the cells to release and dissolve the purple crystals and the optical density of the solution was determined. The results are expressed as percentages with respect to the control, which was set at 100%.

Tissue Culture and Mechanical Conditioning

Three experimental groups of valve leaflet tissues were engineered to compare tissue formation and to show the feasibility of the strain-based approach. The first group comprises rectangular shaped valve leaflet tissue-equivalents. They were cultured statically in a cell culture flask for up to four weeks and could compact freely, serving as non-loaded controls. The second and third group consisted of valve leaflets, all cultured in the DPD. Directly after placement in the DPD, all leaflets were exposed to medium circulation at low speed (4 ml/min) to supply fresh nutrients to the developing tissue. Valve leaflets were cultured up to four weeks, exposed to continuous medium circulation and prestrain due to compaction constrained by the stent (group 2). Additional valve leaflets were exposed to dynamic strains at 1 Hz in addition to the prestrain and continuous medium circulation (group 3). The pressures upstream and downstream of the valves, as well as the dynamic transvalvular pressure, were recorded every three hours. The valve leaflets of group 3 were cultured up to two, three and four weeks. The medium in the medium container, as well as two thirds of the medium in the culture flask, for group 1, was replaced every three to four days.

Evaluation of Tissue Formation

Qualitative Tissue Analysis

Tissue formation in all groups was analyzed by histology after four weeks. Representative pieces were fixed in phosphate-buffered formalin (Fluka, USA) and embedded in paraffin. Sections were cut at 5 $^1$m thickness and studied by Haematoxylin and Eosin (H&E) staining for general tissue morphology and Trichrome Masson staining for collagen formation, as collagen is the main load-bearing component of the extracellular matrix.

Mechanical Testing

The mechanical properties of circumferential strips of the engineered leaflet tissues of the three groups after four weeks of culturing were determined by uniaxial tensile tests. As thickness measurements of the fresh strips are practically difficult, the thickness was determined from representative histology sections. Stress-strain curves were obtained using an uniaxial tensile tester (Instron, Belgium, model 4411, equipped with a load cell of 10 N) with a constant strain rate of 1.7% per second. To get insight into the evolution of mechanical properties in time, the mechanical properties of circumferential strips of dynamically strained leaflets after two and three weeks of culturing were additionally determined.

Estimation of Strains in the Leaflets

To estimate the amount of prestrain in the leaflets, due to compaction constrained by the stent, the difference in size of the leaflets in the stent after culturing and after release from the stent was determined. The leaflets, having an initially bulged shape in the stent, did straighten during culturing due to free compaction of the neo-tissue. The initial circumferential size of the leaflets was 23 mm, whereas in fully straightened leaflets this size was reduced to 20 mm, indicating that the leaflets could compact freely up to 13% during culturing. The circumferential size of the leaflets was measured after release of the leaflets from the stent of the valves exposed to prestrain and medium circulation after four weeks. This measured size was divided by the maximally straightened size of 20 mm to calculate the amount of prestrain in the leaflets. This value was subsequently extracted from 1 and multiplied by 100% to obtain the amount expressed in a percentage of prestrain.

Figure 3:
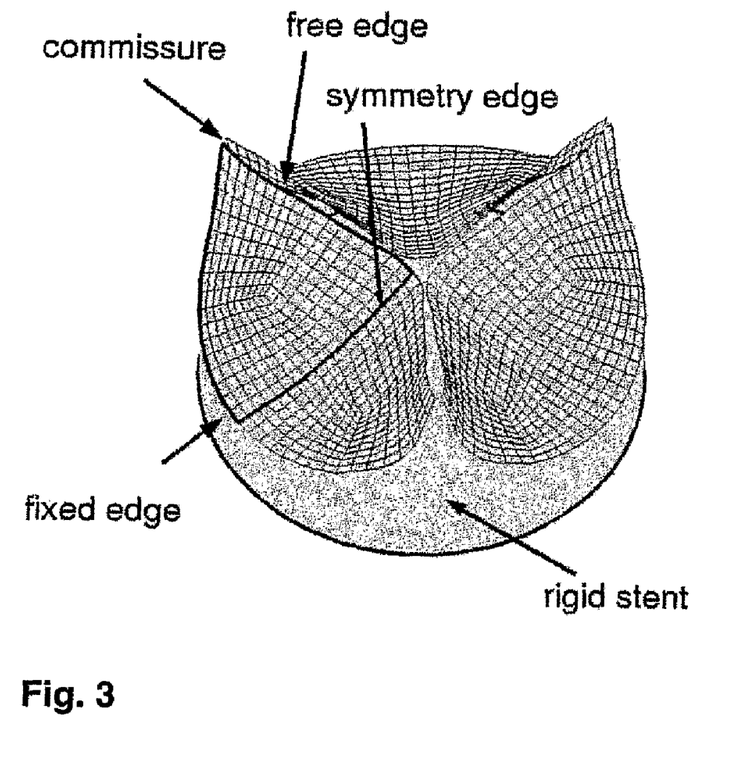
FIG. 3: Finite element mesh of the stented valve geometry. Because of symmetry only ½ of a leaflet is used in the finite element analyses. This part of the geometry is discretized using 224 hexahedral elements.

Finite element analyses were used to estimate the amount and distribution of the dynamic strains in the leaflets resulting from the applied dynamic transvalvular pressure. The finite element mesh of the stented valve geometry is shown in FIG. 3. The configuration shown in this figure was assumed to be stress-free and because of symmetry only ½ of a valve leaflet was used in the finite element analyses. At the symmetry edge, nodal displacements in the normal direction were suppressed, whereas at the fixed edge all nodal displacements were set to zero. At the free edge, a contact surface was defined to model coaptation of adjacent leaflets. The transvalvular pressure ptv was subsequently applied to the downstream surface of the leaflets. In this study, the finite element package SEPRAN was used (Segal, 1984).

The valve tissues were modeled as an incompressible generalized Neo-Hookean material:

$$\sigma = -pI + G(B-I) \tag{1.1}$$

with $\sigma$ the Cauchy stress, p the hydrostatic pressure, I the unity tensor and G the shear modulus of the material. The left Cauchy-Green deformation tensor was defined as $B = F \cdot F^T$ with F the deformation gradient tensor. To describe the (potential) non-linear behavior of the leaflet tissues, the following expression for G was used:

$$G = G0(I_1(B)/3)^n \tag{1.2}$$

with G0 and n material parameters and $I_1(B) = \text{trace}(B)$ the first invariant of B. The parameter of n is used to control the degree of non-linearity: n>0 results in strain hardening, n<0 in strain stiffening and for n=0 the classical Neo-Hookean model is obtained. The material parameters were obtained by fitting the constitutive law (Eq. 1.1) to the mean results before failure of the uniaxial tensile tests of the leaflet tissues exposed to dynamic strains after two, three, and four weeks of culturing.

Results

The DPD

Figure 4:
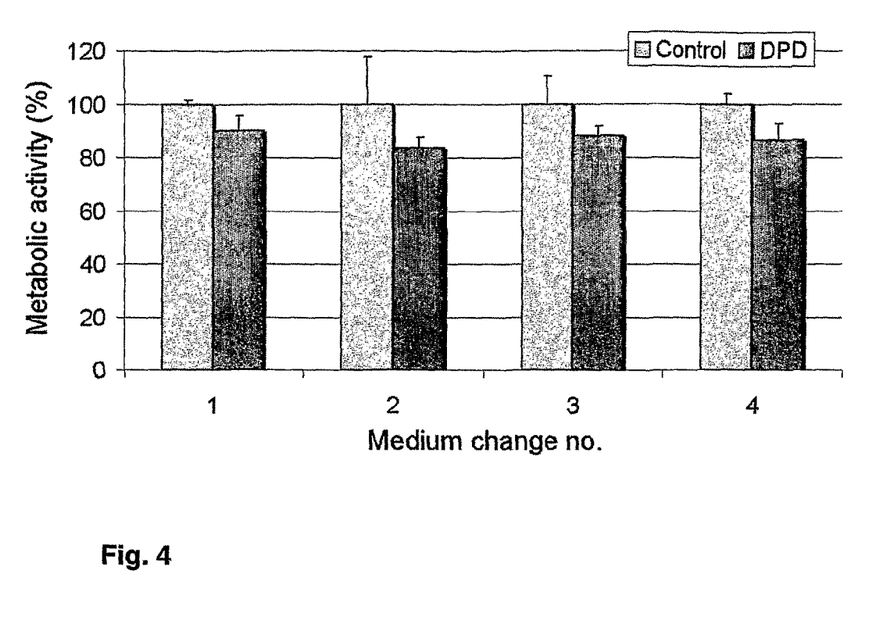
FIG. 4: A graph of the metabolic activity of cells cultured with the first four changes of the medium that has circulated in the DPD during the sterility test.

The tested medium (dark gray bars) was compared to control medium (light gray bars), which were set at 100%. The metabolic activity was in all cases 80-100% compared to the controls and, therefore, the DPD can be considered as being biocompatible. The error bars represent the standard error of the mean.

The medium, without addition of antibiotics, that had circulated in the DPD did not show any macroscopic or microscopic signs of contamination for the complete test period. The system was easy to handle and the risk of contamination during medium replacement was minimal. The results of the biocompatibility test, performed for the first four medium changes during the sterility test, are shown in FIG. 4. The metabolic activity of the cells cultured with the four tested media were all within 80 to 100% when compared to the controls, indicating the DPD to be biocompatible and suitable for cultivation of human heart valves.

Dynamic Straining Protocol

Figure 5:
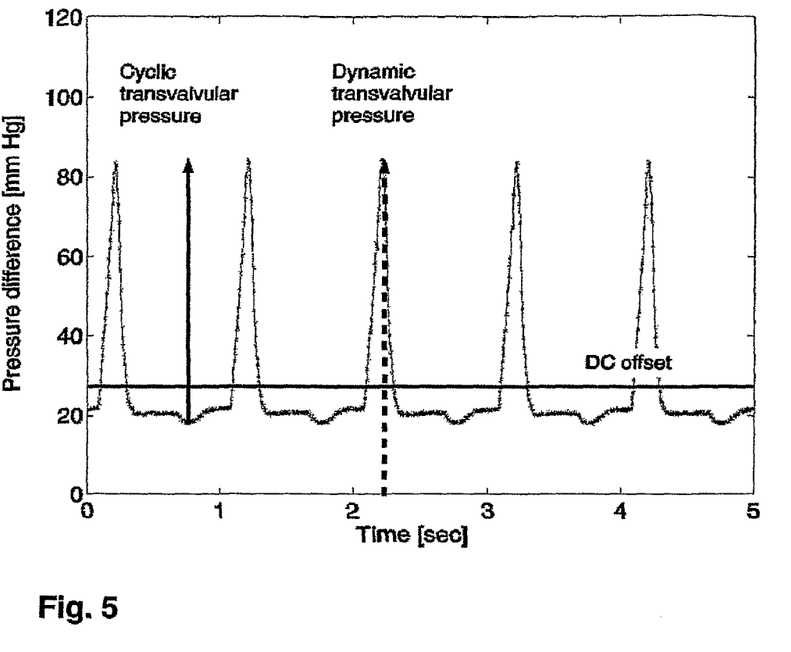
FIG. 5: A representative transvalvular pressure curve measured during culturing of the valves.
Figure 6A:
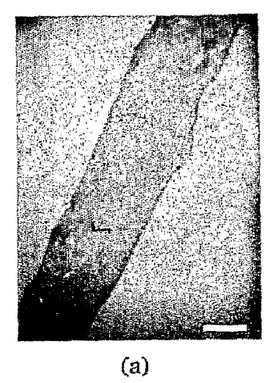
FIGS. 6a, 6b, 6c, 6d, 6e, 6f: Representative sections of the valve leaflet tissues after four weeks of culturing stained with H&E (a,b,c) and Trichrome Masson (d,e,f).
Figure 6B:
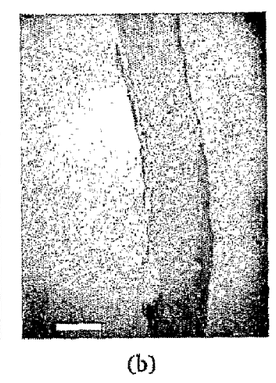
Figure 6C:
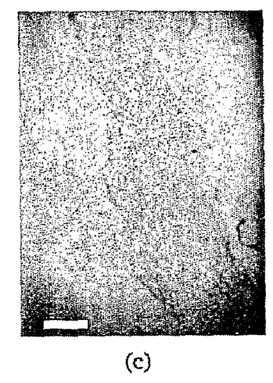
Figure 6D:
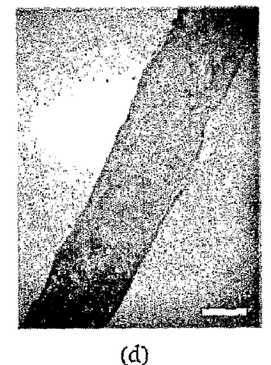
Figure 6E:
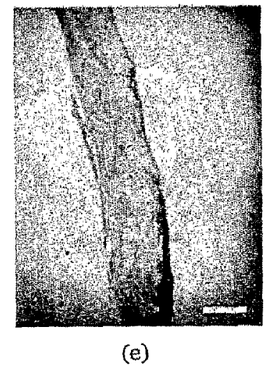
Figure 6F:
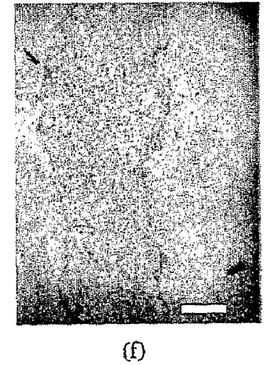

A representative transvalvular pressure curve, measured during culturing is shown in FIG. 5. The definitions of the DC offset, the cyclic transvalvular pressure difference, and the dynamic transvalvular pressure difference are represented. The permanent transvalvular pressure, present over the valve leaflets, is referred to as the DC offset, which is the average value of the difference in pressure upstream and downstream of the valve. The cyclic transvalvular pressure is defined as the peak-to-peak transvalvular pressure value. The maximum transvalvular pressure value, including the DC offset and the cyclic transvalvular pressure, is referred to as the applied dynamic transvalvular pressure.

The dynamic transvalvular pressure was averaged for each day, resulting in dynamic transvalvular pressures increasing gradually from 0 to about 80 mm Hg within the first two weeks of culturing. The last two weeks of culturing, the pressures were lowered, due to the expected loss of the support function of the scaffold, and kept constant at about 37 mm Hg.

Evaluation of Tissue Formation

Histology

Sections stained with H&E and Trichrome Masson (FIG. 6) showed superior tissue formation in the leaflets (FIGS. 6(*a*), 6(*b*), 6(*d*), 6(*e*)) when compared to the non-loaded rectangular leaflet tissue-equivalents (FIGS. 6(*c*), 6(*f*)). The tissue of the leaflets cultured with additional dynamic strains (FIGS. 6(*a*), 5,6(*d*)) appeared to be more homogeneous and denser when compared to the leaflets exposed to prestrain only (FIGS. 6(*b*), 6(*e*)). Collagen could be identified in the leaflets, either cultured using prestrain or additional dynamic strains, after four weeks of culturing (FIGS. 6(*e*), 6(*d*)). The bars in the images represent scales of 350 $^1$m. The dynamically strained leaflets (a,d) and the leaflets exposed to prestrain only (b,e) showed superior tissue development when compared to the non-loaded valve leaflet tissue-equivalents (c,f). The dynamically strained leaflet tissue seemed more homogeneous and denser as compared to the leaflets exposed to prestrain only. Collagen, stained blue, could be identified in the leaflets (d,e).

Mechanical Tests

Figure 7A:
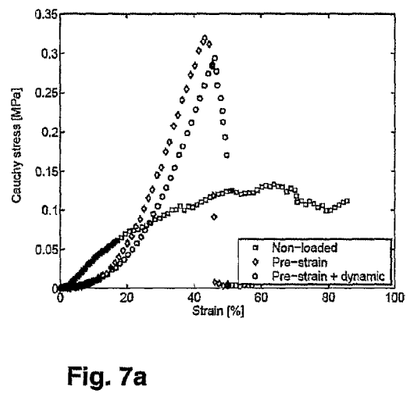
FIGS. 7a, 7b: Stress-strain curves after four weeks of culturing of non-loaded leaflet tissue-equivalents, leaflets exposed to prestrain, and leaflets exposed to additional dynamic strains (a) and the evolution of mechanical properties over time for dynamically strained leaflets (b).
Figure 7B:
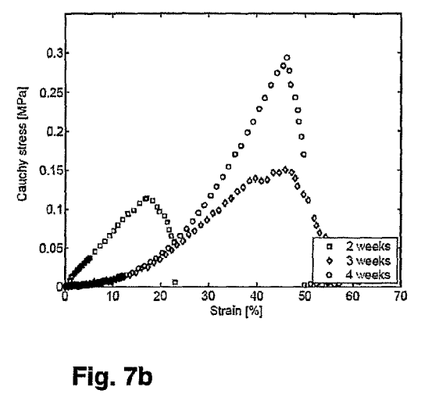

Representative stress-strain curves for all groups after four weeks of culturing are shown in FIG. 7(*a*). The non-loaded leaflet equivalents showed linear behavior, while the leaflets, exposed to compaction-induced prestrain and either with or without additional dynamic strains, showed more tissue-like non-linear behavior after four weeks of culturing (a) The evolution of mechanical properties with increasing culture time is shown in FIG. 7(*b*) for the leaflets exposed to dynamic strains. After two weeks of culturing, the mechanical behavior was linear, representing scaffold-like behavior. After three and four weeks, the tissue showed more non-linear mechanical behavior, representative for tissue contribution.

Estimation of Strains in the Leaflets

Prestrain

The amount of prestrain in the leaflets of the valves exposed to prestrain only after four weeks of culturing, assuming maximal straightening of the leaflets, was shown to vary between 3 and 5%.

Dynamic Strains

Figure 8A:
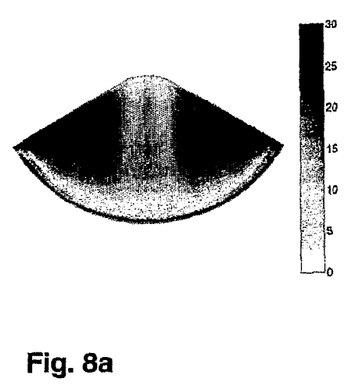
FIGS. 8a, 8b, 8c: A graph of the dynamic strain distribution after four weeks of culturing at the upstream (a) and downstream (b) surfaces of the leaflets at an applied dynamic transvalvular pressure difference of 37 mm Hg. The grayscale represents the amount of dynamic strains in %. The relative amount of the overall dynamic strains found in the leaflet and the mean value are shown in the histogram (c).
Figure 8B:
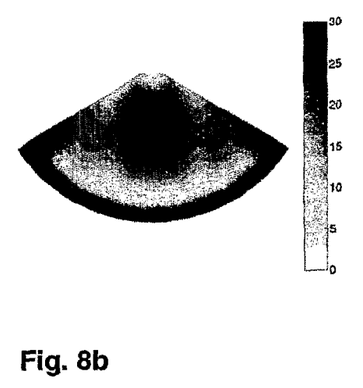
Figure 8C:
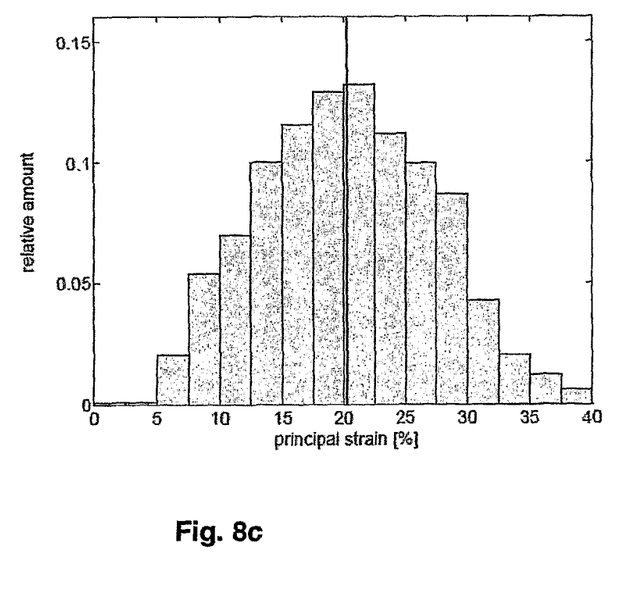

The constitutive law (Eq. 1.1) fitted the results of the uniaxial tensile tests quite reasonable. Table 1.1 summarizes the input parameters for the finite element model, the mean absolute error of the fits, and the estimated mean dynamic strains after two, three and four weeks of culturing, based on a transvalvular pressure difference of 37 mm Hg. The mean dynamic strains in the leaflets increased from 8% after two weeks to about 20% after four weeks of culturing. The dynamic strain distribution in the leaflets after four weeks of culturing is shown in FIGS. 8a,8b,8c, with in FIGS. 8(a) and 8(b) the strain distribution within one leaflet at respectively the upstream and downstream surface and in FIG. 8(c) the estimated range of overall dynamic strains within a leaflet.

TABLE 1.1

Summary of the input parameters for the finite element analyses of the dynamically strained leaflets after two, three, and four weeks of culturing. The parameter n has been set to zero for the leaflets after two weeks of culturing, due to the observed linear behavior. Furthermore, the mean absolute errors of the fits of the constitutive law (Eq. 1.1) to the results of the uniaxial tensile tests and the resulting estimated mean dynamic strains are represented.

| Culture time [weeks] | Thickness [mm] | $G_0$ [kPa] | n [-] | Mean absolute error of fit [kPa] | Mean dynamic strain [%] |
|---|---|---|---|---|---|
| 2 | 0.80 | 188 | 0.0 | 0.95 | 8 |
| 3 | 0.59 | 51 | 8.6 | 3.93 | 24 |
| 4 | 0.63 | 59 | 9.2 | 4.61 | 20 |

DISCUSSION

Mechanical stimulation of tissue formation is a well-known technique in tissue engineering of cardiovascular structures to improve tissue formation and organization. Various conditioning approaches are being employed in bioreactor systems, from flow-based to strain-based to even mimicking the exact physiological environment in the body. For tissue engineering of blood vessels, flow-based as well as strain-based approaches are used, however, for tissue engineering of heart valves, only flow-based approaches have been described. The optimal conditioning protocol depends on several factors, such as the sensitivity of the cell phenotype and source (i.e. animal or human) to mechanical cues, the scaffold used, the transfer of the mechanical cues from the scaffold to the cells, and the magnitude and type of mechanical cue.

If the forms was put on tissue engineering of human heart valve leaflets engineered from human saphenous vein cells seeded using fibrin as a cell carrier onto PGA/P4HB trileaflet heart valve scaffolds (FIGS. 1a,1b). For this particular cell type, being more sensitive to mechanical stimulation as compared to human arterial derived cells, we previously have shown a large impact of cyclic straining during culturing on tissue formation (Mol et al., 2003). In this former study, the amount of extracellular matrix formation increased when larger strains were used. Flow is most likely not necessitated in the early phase of tissue development, but might start to play a significant role as soon as the leaflets are to be seeded with endothelial cells in a later phase. Flow might then stabilize the tissue via signaling by the endothelial cells and prepare the tissue for subsequent implantation. This study describes a strain-based approach to tissue engineer human heart valve leaflets. In order to expose the developing heart valve leaflets to dynamic strains, a pressure difference had to be applied over the leaflets, mimicking the diastolic phase in the heart. A novel bioreactor, the Diastolic Pulse Duplicator (FIGS. 2a,2b), is developed for this purpose, which can expose the developing tissue to increasing amounts of dynamic strains. Besides application of dynamic strains, the leaflets cultured in this study were exposed to prestrain, due to tissue compaction constrained by the stented geometry. The flow was kept low (4 ml/min) and served solely to provide the tissue with sufficient fresh nutrients and to remove waste products. The DPD was very easy to handle, sized small with a total medium volume of only 75 ml per valve, proven to be biocompatible (FIG. 4), and sterility could be maintained over prolonged periods of time.

Rectangular non-loaded valve leaflet tissue-equivalents were shown to render much less tissue formation after four weeks of culturing when compared to the superior tissue formation in the leaflets, exposed to either prestrain only as well as to additional dynamic strains (FIG. 6). The tissue of the leaflets exposed to dynamic strains appeared to be more homogeneous and denser packed as compared to leaflets exposed to prestrain only, however, this concerned only qualitative observations by histology. The mechanical properties (FIGS. 7a,7b) of the leaflets exposed to dynamic strains showed increased non-linear tissue-like behavior over time, indicating increasing amounts of tissue and collagen. After four weeks of culturing, the non-loaded rectangular shaped leaflet tissue-equivalents showed linear behavior, representative for scaffold behavior. The leaflets, exposed to prestrain alone as well as to additional dynamic strains showed non-linear behavior after four weeks of culturing, correlating with the larger amounts of tissue found in the leaflets as compared to the non-loaded leaflet tissue-equivalents. The continuous medium circulation in the DPD will most likely contribute to the improved tissue formation in the leaflets as well.

Prestrain alone obviously resulted in abundant amounts of tissue. The prestrain is estimated to be in the range of 3 to 5% and might already be sufficient for optimized tissue formation. However, dynamic straining might further enhance tissue organization and, furthermore, might represent a valuable tool to maintain the bulged shape of the leaflets by some deformation of the scaffold and the tissue. Furthermore, for future applications towards tissue engineering of stentless human heart valves, dynamic strains will be of larger importance as the prestrains in stentless valves will be much less.

To get insight into the amount of dynamic strains applied to the leaflets, the dynamic strain distribution was estimated. The material properties of the leaflets determine the amount of dynamic strains at a given dynamic transvalvular pressure. The transvalvular pressure was monitored in the DPD during culturing (FIG. 5). Theoretically, the amount of dynamic strains can be monitored using markers on the leaflets and subsequent imaging of the leaflets being strained, followed by image analyses. As this is a time-consuming and in practice rather difficult method, we have chosen to estimate the dynamic strains in the leaflets by finite element analyses. The material parameters of the developing leaflets, determined by fitting the constitutive law (Eq. 1.1) to the mean results of the uniaxial tensile tests before failure, were used to serve as input for the finite element analyses. The mean dynamic strain in the valve leaflets cultured in this study, as an example for future use, were estimated to vary from 8% at two weeks to 20% at four weeks of culturing (FIGS. 8a,8b,8c and Table 1.1). The estimated dynamic strains increased between week two and three, while the applied dynamic transvalvular pressures were similar, indicating loss of scaffold support, resulting in a decreased stiffness of the tissues, as shown by a lower shear modulus after three weeks of culturing. For the stented valve geometry, the amount of applied dynamic strains in this study might be too large for optimized tissue formation, when taking the prestrain into account, but application of large dynamic strains in the DPD was shown feasible. As currently the strains in the leaflets are determined afterwards, a future research focus for optimization of the Diastolic Pulse Duplicator is the development of a non-invasive method to determine tissue strains directly during culturing and to integrate this feature in a feedback loop to control the magnitude of the strains.

In the finite element analysis, an initial stress-free configuration of the leaflets is assumed, which is not completely true as the valve leaflets show compaction during culturing. The material properties of the leaflets are assumed to be homogeneous and isotropic, which might not be the case after a certain culture period due to the influence of prestrain in mainly the circumferential direction and the local dynamic strain distribution in the leaflets. Therefore, leaflets to be cultured in the DPD will be mechanically tested in both circumferential and radial direction to identify possible anisotropic properties. In case of anisotropic properties, an extended model should be used for the finite element analyses as described by Driessen et al. (2004).

REFERENCES

Barron, V., Lyons, E., Stenson-Cox, C., McHugh, P. E., and Pandit, A. (2003). Bioreactors for cardiovascular cell and tissue growth: a review. *Annals of biomedical engineering*, 31, 1017-1030.

Chapman, G. B., Durante, W., Hellums, J. D., and Schafer, A. I. (2000). Physiological cyclic stretch causes cell cycle arrest in cultured vascular smooth muscle cells. *American journal of physiology. Heart and circulatory physiology*, 278, H748-H754.

Dethlefsen, S. M., Shepro, D., and D'Amore, P. A. (1996). Comparison of the effects of mechanical stimulation on venous and arterial smooth muscle cells in vitro. *Journal of vascular research*, 33, 405-413.

Driessen, N. J. B., Bouten, C. V. C., and Baaijens, F. P. T. (2004). A structural constitutive model for collagenous cardiovascular tissue incorporating the angular fiber distribution. *Journal of biomechanical engineering*, Dumont, K., Yperman, J., Verbeken, E., Segers, P., Meuris, B., Vandenberghe, S., Flameng, W., and Verdonck, P. R. (2002). Design of a new pulsatile bioreactor for tissue engineered aortic heart valve formation. *Artificial organs*, 26, 710-714.

Engelmayr, G. C., Rabkin, E., Sutherland, F. W. H., Schoen, F. J., Mayer, J. E., and Sacks, M. S. (2005). The independent role of cyclic flexure in the early in vitro development of an engineered heart valve tissue. *Biomaterials*, 26, 175-187.

Gonen-Wadmany, M., Gepstein, L., and Seliktar, D. (2004). Controlling the cellular organization of tissue engineered cardiac constructs. *Annals of the New York academy of sciences*, 1015, 299-311.

Hildebrand, D. K., Wu, Z. J., Mayer, J. E., and Sacks, M. S. (2004). Design and hydrodynamic evaluation of a novel pulsatile bioreactor for biologically active heart valves. *Annals of biomedical engineering*, 32, 1039-1049.

Hoerstrup, S. P., Sodian, R., Daebritz, S., Wang, J., Bacha, E. A., Martin, D. P., Moran, A. M., Guleresian, J., Sperling, J. S., Kaushal, S., Vacanti, J. P., Schoen, F. J., and Mayer, J. E. (2000a). Functional living trileaflet heart valves grown in vitro. *Circulation*, 102 (suppl III), III49-III49.

Hoerstrup, S. P., Kadner, A., Breymann, C., Maurus, C. F., Guenter, C. I., Sodian, R., Visjager, J. F., Zund, G., and Turina, M. I. (2002a). Living, autologous pulmonary artery conduits tissue engineered from human umbilical cord cells. *Annals of thoracic surgery*, 74, 46-52.

Hoerstrup, S. P., Zund, G., Cheng, S., Melnitchouk, S., Kadner, A., Sodian, R., Kolb, S. A., and Turina, M. (2002b). A new approach to completely autologous cardiovascular tissue in humans. *ASAIO journal*, 48, 234-238.

Jockenhoevel, S., Zund, G., Hoerstrup, S. P., Schnell, A., and Turina, M. (2002). Cardiovascular tissue engineering: a new laminar flow chamber for in vitro improvement of mechanical tissue properties. *ASAIO journal*, 48, 8-11.

Kim, B., Nikolovski, J., Bonadio, J., and Mooney, D. J. (1999). Cyclic mechanical strain regulates the development of engineered smooth muscle tissue. *Nature biotechnology*, 17, 979-983.

Kim, B. and Mooney, D. J. (2000). Scaffolds for engineering smooth muscle under cyclic mechanical strain conditions. *Journal of biomechanical engineering*, 122, 210-215.

Lee, A. A., Graham, D. A., Cruz, S. D., Ratcliffe, A., and Karlon, W. J. (2002). Fluid shear stress-induced alignment of cultured smooth muscle cells. *Journal of biomechanical engineering*, 124, 37-43.

McCulloch, A. D., Harris, A. B., Sarraf, C. E., and Eastwood, M. (2004). New multi-cue bioreactor for tissue engineering of tubular cardiovascular samples under physiological conditions. *Tissue engineering*, 10, 565-573.

Mironov, V., Kasayanov, V., McAllister, K., Oliver, S., Sistino, J., and Markwald, R. (2003). Perfusion bioreactor for vascular tissue engineering with capacities for longitudinal stretch. *Journal of craniofacial surgery*, 14, 340-347.

Mol, A., Bouten, C. V. C., Zund, G., Guenter, C. I., Visjager, J. F., Turina, M., Baaijens, F. P. T., and Hoerstrup, S. P. (2003). The relevance of large strains in functional tissue engineering of heart valves. *Thoracic and cardiovascular surgeon*, 51, 78-83.

Mol, A., van Lieshout, M. I., dam de Veen, G. C., Neuenschwander, S., Hoerstrup, S. P., Baaijens, F. P. T., and Bouten, C. V. C. (2005). Fibrin as a cell carrier in cardiovascular tissue engineering applications. *Biomaterials*, 26, 3113-3121.

Mosmann, T. (1983). Rapid calorimetric assay for cellular growth and survival: application to proliferation and cytotoxicity assays. *Journal of immunological methods*, 65, 55-63.

Nackman, G. B., Fillinger, M. F., Shafritz, R., Wei, T., and Graham, A. M. (1998). Flow modulates endothelial regulation of smooth muscle cell proliferation: a new model. *Surgery*, 124, 353-361.

Narita, Y., Hata, K., H. K., Usui, A., Ueda, M., and Ueda, Y. (2004). Novel pulse duplicating bioreactor system for tissue-engineered vascular constructs. *Tissue engineering*, 10, 1224-1233.

Niklason, L. E., Gao, J., Abbott, W. M., Hirschi, K. K., Houser, S., Marini, R., and Langer, R. (1999). Functional arteries grown in vitro. *Science*, 284, 489-493.

Niklason, L. E., Abott, W., Gao, J., Klagges, B., Hirschi, K. K., Ulubayram, K., Conroy, N., Jones, R., Vasanawala, A., Sanzgiri, S., and Langer, R. (2001). Morphological and mechanical characteristics of engineered bovine arteries. *Journal of vascular surgery*, 33, 628-638.

O'Callaghan, C. J. and Williams, B. (2000). Mechanical strain induced extracellular matrix production by human vascular smooth muscle cells: Role of tgf-beta. *Hypertension*, 36, 319-324.

Rutten, M. C. M., Wijlaars, M. W., Mol, A., van Dam, E. A., Strijkers, G. J., Nicolay, K., and Baaijens, F. P. T. (2005).

The valve exerciser: a novel bioreactor for physiological loading of tissue-engineered aortic valves. *Journal of biomechanics*.

Schnell, A. M., Hoerstrup, S. P., Zund, G., Kolb, S., Sodian, R., Visjager, J. F., Grunenfelder, J., Suter, A., and Turina, M. (2001). Optimal cell source for tissue engineering: Venous vs. aortic human myofibroblasts. *Thoracic and cardiovascular surgeon*, 49, 221-225.

Segal, A. (1984). SEPRAN user manual, standard problems and programmers guide. Leidschendam: Ingenieursbureau SEPRA, the Netherlands.

Seliktar, D., Black, R. A., Vito, R. P., and Nerem, R. M. (2000). Dynamic mechanical conditioning of collagen-gel blood vessel constructs induces remodeling in vitro. *Annals of biomedical engineering*, 28, 351-62.

Sodian, R., Lemke, T., Loebe, M., Hoerstrup, S. P., Potapov, E. V., Hausmann, H., Meyer, R., and Hetzer, R. (2001). New pulsatile bioreactor for fabrication of tissue-engineered patches. *Journal of biomedical materials research*, 58, 401-405.

Sodian, R., Lemke, T., Fritsche, C., Hoerstrup, S. P., Fu, P., Potapov, E. V., Hausmann, H., and Hetzer, R. (2002b). Tissue-engineering bioreactors: a new combined cell-seeding and perfusion system for vascular tissue engineering. *Tissue engineering*, 8, 863-870.

Thompson, C. A., Colon-Hernandez, P., Pomerantseva, I., MacNeil, B. D., Nasseri, B., Vacanti, J. P., and Oesterle, S. N. (2002). A novel pulsatile, laminar flow bioreactor for the development of tissue engineered vascular structures. *Tissue engineering*, 8, 1083-1088.

Ueba, H., Kawakami, M., and Yaginuma, T. (1997). Shear stress as an inhibitor of vascular smooth muscle cell proliferation: Role of transforming growth factor-beta1 and tissue-type plasminogen activator. *Arteriosclerosis, thrombosis, and vascular biology*, 17, 1512-1516.

Watase, M., Awolesi, M. A., Ricotta, J., and Sumpio, B. E. (1997). Effects of pressure on cultured smooth muscle cells. *Life sciences*, 61, 987-996.

Weston, M. W. and Yoganathan, A. P. (2001). Biosynthetic activity in heart valve leaflets in response to in vitro flow environments. *Annals of biomedical engineering*, 29, 752-763.

Williams, C. and Wick, T. M. (2004). Perfusion bioreactor for small diameter tissue-engineered arteries. *Tissue engineering*, 10, 930-941.

The invention claimed is:

1. A method of manufacturing a tissue-engineered prosthesis having at least in an open condition a flow passage, wherein the prosthesis is a heart valve, comprising the steps of:

placing a seeded 3D scaffold in a bioreactor chamber, providing at least one perfusion flow of a nutrient medium in the bioreactor chamber to supply said seeded 3D scaffold and/or a thereon developing tissue with nutrients, wherein the at least one perfusion flow has substantially no pulsation and whereby a flow passage of the seeded 3D scaffold and/or the thereon developing tissue in relation to the flow passage of the finished prosthesis is restricted or zero during tissue development during the duration stay in the bioreactor chamber, and wherein the at least one perfusion flow is less than 50 ml/min, applying in addition a dynamic pressure difference with a frequency of 0.1 to 10 Hz over the 3D scaffold and/or thereon developing tissue depending on the condition and/or stage of tissue development to create strain in the 3D scaffold and/or thereon developing tissue by restricting or closing the flow passage of the developing prosthesis during the duration stay in the bioreactor chamber, wherein the dynamic pressure difference is a difference in pressure upstream and downstream of the restricted flow passage, removing the 3D scaffold from the bioreactor chamber, and subsequently opening the restricted or zero flow passage to its finished size, wherein the restricted or zero flow passage is at least 20% smaller than the flow passage of the finished prosthesis.

2. The method of claim 1, wherein the prosthesis is a heart valve having leaflets and the restriction is achieved by coaptation of the leaflets.

3. The method of claim 1, wherein the restricted or zero flow passage is at least 50%, smaller than the flow passage of the finished prosthesis.

4. The method of claim 1, wherein the at least one perfusion flow is less than 5 ml/min.

5. The method of claim 1, wherein the pressure difference is substantially zero at the beginning, subsequently increasing up to a mean peak pressure difference and thereafter decreasing to the end of the duration of stay of the 3D scaffold and/or thereon developing tissue in the bioreactor chamber.

6. The method of claim 1 wherein a mean peak pressure difference averaged for 24 hours, is above 25 mmHg, preferably above 45 mmHg.

7. The method of claim 1, wherein the mean pressure difference over a time period, which is 30-70%, preferably 45-55%, of the duration of stay in the bioreactor, is substantially zero.

8. The method of claim 7, wherein the mean peak pressure difference averaged for 24 hours is reached after 60%, preferably after 70%, of the duration of stay in the bio-reactor.

9. The method of claim 8 wherein the modulated pressure differences per time period, preferably 24 hours, are used to provide respective strain distribution in that time period.

10. The method of claim 1, wherein the dynamic pressure difference has a frequency of 1 Hz.

* * * * *